United States Patent
Shen et al.

(10) Patent No.: US 12,023,649 B2
(45) Date of Patent: Jul. 2, 2024

(54) PLANT LEAVES-DERIVED CARBON MATERIAL DOPED WITH TWO METALS AND PREPARATION AND USE THEREOF

(71) Applicant: Zhejiang University of Technology, Hangzhou (CN)

(72) Inventors: Haimin Shen, Hangzhou (CN); Dong Lv, Hangzhou (CN)

(73) Assignee: Zhejiang University of Technology, Hangzhou (CN)

( * ) Notice: Subject to any disclaimer, the term of this patent is extended or adjusted under 35 U.S.C. 154(b) by 134 days.

(21) Appl. No.: 17/811,221

(22) Filed: Jul. 7, 2022

(65) Prior Publication Data

US 2023/0069145 A1    Mar. 2, 2023

(30) Foreign Application Priority Data

Aug. 25, 2021    (CN) .......................... 202110980994.8

(51) Int. Cl.
| | | |
|---|---|---|
| *B01J 21/18* | (2006.01) | |
| *B01J 23/06* | (2006.01) | |
| *B01J 23/34* | (2006.01) | |
| *B01J 23/72* | (2006.01) | |
| *B01J 23/745* | (2006.01) | |
| *B01J 23/75* | (2006.01) | |
| *B01J 23/755* | (2006.01) | |
| *B01J 37/00* | (2006.01) | |
| *B01J 37/04* | (2006.01) | |
| *B01J 37/06* | (2006.01) | |
| *C07C 27/12* | (2006.01) | |

(52) U.S. Cl.
CPC .............. *B01J 21/18* (2013.01); *B01J 23/06* (2013.01); *B01J 23/34* (2013.01); *B01J 23/72* (2013.01); *B01J 23/745* (2013.01); *B01J 23/75* (2013.01); *B01J 23/755* (2013.01); *B01J 37/0036* (2013.01); *B01J 37/04* (2013.01); *B01J 37/06* (2013.01); *C07C 27/12* (2013.01); *C07C 2521/18* (2013.01); *C07C 2523/06* (2013.01); *C07C 2523/34* (2013.01); *C07C 2523/72* (2013.01); *C07C 2523/745* (2013.01); *C07C 2523/75* (2013.01); *C07C 2523/755* (2013.01)

(58) Field of Classification Search
CPC ... B01J 21/18; B01J 23/06; B01J 23/34; B01J 23/72; B01J 23/745; B01J 23/75; B01J 23/755; B01J 23/80; B01J 23/8892; B01J 37/0036; B01J 37/0201; B01J 37/04; B01J 37/06; B01J 37/084; B01J 37/088; C07C 27/12; C07C 29/50; C07C 45/33; C07C 2521/18; C07C 2523/06; C07C 2523/34; C07C 2523/72; C07C 2523/745; C07C 2523/75; C07C 2601/08; C07C 2601/14; C07C 2601/18; C07C 2601/20; C07C 2523/755
See application file for complete search history.

(56) References Cited

FOREIGN PATENT DOCUMENTS

CN    105289496    *    2/2016    ............... B01J 20/20

OTHER PUBLICATIONS

Google Machine Translation of CN105289496 (Year: 2016).*
WIPO Machine Translation of CN105289496 (Year: 2016).*

* cited by examiner

*Primary Examiner* — Brian A McCaig
(74) *Attorney, Agent, or Firm* — Neal, Gerber & Eisenberg LLP

(57) ABSTRACT

A plant leaves-derived carbon material doped with two metals and preparation and use thereof are provided, the carbon material prepared by carbonizing, in an inert atmosphere, plant leaves which have absorbed ions of two metals M1 and M2. The metal M1 is Co, Mn, or Fe. The metal M2 is Ni, Cu, or Zn. The carbon material can be used as an efficient, green, and safe catalyst for the selective oxidation of cycloalkanes to produce cycloalkanols and cycloalkanones, and enable an increased selectivity of the target products (thus less by-products), a low yield of cycloalkyl peroxides, reduced reaction temperature, low environmental impact, and safe production.

8 Claims, No Drawings

PLANT LEAVES-DERIVED CARBON MATERIAL DOPED WITH TWO METALS AND PREPARATION AND USE THEREOF

CROSS REFERENCE TO RELATED APPLICATION

This patent application claims the benefit and priority of Chinese Patent Application No. 202110980994.8, filed on Aug. 25, 2021, the disclosure of which is incorporated by reference herein in its entirety as part of the present application.

TECHNICAL FIELD

The present disclosure is related to the fields of catalysis and organic synthesis, and, in particular, to a plant leaves-derived carbon material doped with two metals and preparation and use thereof.

BACKGROUND ART

Catalytic oxidation of cycloalkanes to cycloalkanols and cycloalkanones is an important industrial process. It is well known that cycloalkanols and cycloalkanones are not only important organic solvents, but also important intermediates in preparation of pesticides, pharmaceuticals, dyes, surfactants, resins, and other fine chemicals, especially nylon 6 and nylon 66. Currently, the oxidation of cycloalkanes is usually conducted at a temperature of 150 to 170° C. using a homogeneous cobalt (II) or manganese (II) salt as a catalyst and molecular oxygen as an oxidant. However, the process has problems in that it requires high temperature and exhibits low substrate degree of conversion and low selectivity of the target products and it is difficult for the process to suppress formation of aliphatic diacids (Applied Catalysis A, General 2019, 575:120-131; Catalysis Communications 2019, 132:105809). These problems mainly arise from: 1) uncontrolled diffusion of free radicals that are involved in the oxidation of cycloalkanes in the reaction system, and 2) cycloalkyl hydroperoxide, an intermediate oxidation product, which is thermally decomposed to free radicals and then converted into the target products cycloalkanol and cycloalkanone in an uncontrolled manner, causing the reaction to be harder to control and leading to lower selectivities of the target products. Therefore, it would be advantageous to effectively control diffusion of the free radicals in the reaction system and to promote catalytic conversion of cycloalkyl hydroperoxide into cycloalkanol and cycloalkanone to improve their selectivities. This is expected to drastically improve the process for the catalytic oxidation of cycloalkanes.

Plant leaves are known to have a highly porous structure and a high specific surface area. Carbon materials produced by carbonizing plant leaves can retain the highly porous structure and high specific surface area of the leaves and can act as a carrier material for catalytically active substances. In this regard, the present disclosure proposes a plant leaves-derived carbon material doped with two metals. The two metals are strongly and stably supported on the plant leaves-derived carbon material which acts as a carrier. In addition, the porous structure of the carbon material may define a confined environment and suppress the uncontrolled diffusion of the free radicals that are involved in the oxidation of cycloalkanes. The introduction of the two metals into the carbon material can prevent uncontrolled decomposition of cycloalkyl hydroperoxide (which is an intermediate oxidation product formed during the oxidation of cycloalkane, as described above) and promote the conversion of cycloalkyl hydroperoxide into cycloalkanol and cycloalkanone, leading to increased selectivities of the target products. Moreover, the oxidation capacity of cycloalkyl hydroperoxide can be fully utilized, so the degree of conversion of the substrate can also be increased and the selectivities of the target products can be further increased. The plant leaves-derived carbon material doped with two metals proposed by the present disclosure has been found to be an efficient, green, and safe catalyst for the selective oxidation of cycloalkanes by means of oxygen to produce cycloalkanols and cycloalkanones, and to enable increased selectivities of the target products (thus less by-products), reduced reaction temperature, and low environmental impact.

SUMMARY

Therefore, among the objectives of the present disclosure are to provide a plant leaves-derived carbon material doped with two metals and a preparation method thereof as well as use thereof as a catalyst for the oxidation of cycloalkanes by means of molecular oxygen. The plant leaves-derived carbon material doped with two meals according to the present disclosure is produced by carbonizing plant leaves which have absorbed ions of two different metals. It is found that such a carbon material has more micropores than conventional carbon materials and exhibits an advantageous pore size distribution. Such porous structure of the carbon material according to the present disclosure can provide a confined environment and suppress the uncontrolled diffusion of free radicals that are involved in the reaction taking place in the material, thereby resulting in an improved catalytic performance of the material. Moreover, a synergistic effect of the two metals doped in the material has been observed, which leads to a higher catalytic activity and selectivity of the material than any single metal catalyst. In the case where the carbon material according to the present disclosure is used as a catalyst for the oxidation of cycloalkanes by means of oxygen to produce cycloalkanols and cycloalkanones, selectivities of the target products can be improved, resulting in less by-products. This can reduce pollution emissions, and facilitate realization of a continuous industrial process and separation and purification of the products.

The first objective of the present disclosure is realized by a plant leaves-derived carbon material doped with two metals, which is prepared by carbonizing, in an inert atmosphere, plant leaves which have absorbed ions of two metals M1 and M2. The metal M1 is Co, Mn, or Fe. The metal M2 is Ni, Cu, or Zn.

The second objective of the present disclosure is realized by a method for preparing the plant leaves-derived carbon material doped with two metals as described above, the method comprising: immersing a bottom of a branch with the plant leaves in an aqueous solution of metal salts of the metals M1 and M2 for a period of time, followed by removal of the leaves from the branch and washing with fresh water; carbonizing the leaves in a nitrogen atmosphere, followed by cooling the carbonized leaves to room temperature and then grinding the carbonized leaves after being cooled to a powder; washing the powder by stirring the powder in a volume of a hydrochloric acid (HCl) solution in order to remove inorganic salts therefrom, followed by suction filtration, washing until neutral with water, and drying.

In an embodiment, the plant leaves are derived from at least one tree selected from the group consisting of weeping willow (*Salix babylonica*), Chinese parasol tree (*Firmiana*

*simplex*), *Magnolia denudata, Osmanthus*, sweet viburnum (*Viburnum odoratissimum*), *Ginkgo biloba, Populus* L., *Metasequoia glyptostroboides*, and the like.

In an embodiment, M1 is Co (II), Mn (II), or Fe (II). In an embodiment, M2 is Ni (II), Cu (II), or Zn (II). Co (II) may be provided by any one of, or a mixture of any two or more at any ratio of, $Co(CH_3COO)_2$, $Co(NO_3)_2$, $CoSO_4$, $CoCl_2$, and their hydrates. Mn (II) may be provided by any one of, or a mixture of any two or more at any ratio of, $Mn(CH_3COO)_2$, $Mn(NO_3)_2$, $MnSO_4$, $MnCl_2$, and their hydrates. Fe (II) may be provided by any one of, or a mixture of any two or more at any ratio of, $Fe(CH_3COO)_2$, $Fe(NO_3)_2$, $FeSO_4$, $FeCl_2$, and their hydrates. Ni (II) may be provided by any one of, or a mixture of any two or more at any ratio of, $Ni(CH_3COO)_2$, $Ni(NO_3)_2$, $NiSO_4$, $NiCl_2$, and their hydrates. Cu (II) may be provided by any one of, or a mixture of any two or more at any ratio of, $Cu(CH_3COO)_2$, $Cu(NO_3)_2$, $CuSO_4$, $CuCl_2$, and their hydrates. Zn (II) may be provided by any one of, or a mixture of any two or more at any ratio of, $Zn(CH_3COO)_2$, $Zn(NO_3)_2$, $ZnSO_4$, $ZnCl_2$, and their hydrates.

In an embodiment, the aqueous solution of metal salts of the metals M1 and M2 has a concentration of the salt of the metal M1 varying from 0.000001 to 0.001 mol/L, preferably 0.00001 to 0.001 mol/L, and a concentration of the salt of the metal M2 varying from 0.000001 to 0.001 mol/L, preferably 0.00001 to 0.001 mol/L.

In an embodiment, the bottom of the branch is immersed in the aqueous solution of metal salts of the metals M1 and M2 for 1.0 to 48.0 h, preferably 24.0 to 48.0 h. In an embodiment, the leaves removed from the branch is carbonized at 300 to 1000° C. for 1.0 to 5.0 h. In an embodiment, the HCl solution used to wash the powder is at a concentration of 1.0 to 5.0 mol/L. In an embodiment, the powder is washed by stirring it in the HCl solution for 4.0 to 12.0 h.

The third objective of the present disclosure is realized by a process for using the plant leaves-derived carbon material doped with two metals, as described above, to catalyze the oxidation of a cycloalkane to produce cycloalkanol and cycloalkanone, comprising: dispersing the carbon material in the cycloalkane to form a mixture followed by sealing; heating the mixture with stirring to a reaction temperature followed by introducing an oxidant thereinto and stirring for a period of time to allow an oxidation reaction to proceed; and, after completion of the reaction, cooling the reaction mixture to room temperature, followed by addition of triphenylphosphine (pph3) and stirring at room temperature for 30 to 40 min to allow a peroxide formed during the oxidation reaction to be reduced.

The cycloalkane may be any one of, or a mixture of any two or more at any ratio of, cyclopentane, cyclohexane, cycloheptane, cyclooctane, cyclononane, cyclodecane, and cyclododecane.

The oxidant used may be oxygen, air, or a mixture thereof at any ratio.

In an embodiment, the oxidation reaction is conducted at a pressure of 0.1 to 2.0 MPa, preferably 0.5 to 2.0 MPa, and a temperature of 80 to 160° C., preferably 100 to 160° C., for 2.0 to 24.0 h, preferably 8.0 to 24.0 h, with a stirring speed of 600 to 1200 rpm.

In an embodiment, the ratio of the molar amount in mmol of the cycloalkane to the mass in mg of the carbon material is in a range of 5 to 20, preferably 8 to 12.

In an embodiment, pph3 is used in an amount of 2 to 4% by mole, with respect to the total amount of the cycloalkane. The oxidation reaction of the cycloalkane with the oxidant may produce a small amount of a peroxide, and pph3 may reduce the peroxide to cycloalkanol. In this way, the selectivity of the cycloalkanol product is increased.

The method according to the present disclosure comprises a step of immersing a bottom of a branch with the plant leaves in an aqueous solution of metal salts of the metals M1 and M2 for a period of time. In this step, ions of the two metals M1 and M2 can be delivered to the plant leaves, and the leaves can remain intact. Such leaves, after carbonization, have been found to exhibit favourable catalytic activity for the oxidation of cycloalkanes. We have also found that, when the leaves are directly immersed in the aqueous solution of metal salts of the metals M1 and M2, considerable dehydration of the leaves can be observed and they also tend to rot. In this case, the carbon material obtained by carbonizing these leaves has been found to have poor morphology and fail to exhibit good catalytic activity for the oxidation of cycloalkanes.

The present disclosure provides several advantages. A plant leaves-derived carbon material doped with two metals is provided herein, which can be used as a catalyst for the selective oxidation of cycloalkanes with molecular oxygen. The carbon material according to the present disclosure can be prepared sustainably in a simple way at low cost. By using the carbon material according to the present disclosure as a catalyst for the oxidation of cycloalkanes, the target products, cycloalkanols and cycloalkanones, can be produced with high selectivity, resulting in less by-products. Such a catalyst can also enable reduced reaction temperature and low environmental impact. Therefore, the carbon material according to the present disclosure is a novel catalyst for the oxidation of cycloalkanes and exhibits excellent catalytic activity. By using such a carbon material, an efficient, green, and safe process for the catalytic oxidation of cycloalkanes to cycloalkanols and cycloalkanones is realized.

DETAILED DESCRIPTION OF THE EMBODIMENTS

The disclosure will now be further illustrated by the following examples which are not intended to limit the scope of the disclosure in any way.

All reagents and materials used in the examples were of analytical purity.

Examples 1 to 29 illustrate the preparation of the plant leaves-derived carbon material doped with two metals according to the present disclosure.

Examples 30 to 52 illustrate use of the carbon material according to the present disclosure as a catalyst for the selective oxidation of cycloalkanes with molecular oxygen.

Examples 53 and 54 are Comparative Examples.

The experiment in Example 55 was conducted on a larger scale.

Example 1

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 8 h at room temperature, followed by suction filtration, washing until neutral with water, and vacuum drying at 100° C. for 2.0 h. As a result, a weeping willow leaves-derived carbon material doped with two metals, C—Co&Cu$_{0.0001\text{-}24.0}$-700-2.0-2.0-8.0 (immersion in a 0.0001 mol/L solution of salts of Co (II) and Cu (II) for 24 h, carbonization at 700° C. for 2.0 h, and washing with 2.0 mol/L HCl for 8.0 h), was obtained in an amount of 0.6871 g.

Example 2

A bottom of a branch with leaves of a Chinese parasol tree (*Firmiana simplex*) was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a Chinese parasol tree leaves-derived carbon material doped with two metals, C—Co&Cu$_{0.0001\text{-}24.0}$-700-2.0-2.0-8.0 (immersion in a 0.0001 mol/L solution of salts of Co (II) and Cu (II) for 24 h, carbonization at 700° C. for 2.0 h, and washing with 2.0 mol/L HCl for 8.0 h), was obtained in an amount of 0.6648 g.

Example 3

A bottom of a *Magnolia denudata* branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 8 h at room temperature, followed by suction filtration, washing until neutral with water, and vacuum drying at 100° C. for 2.0 h. As a result, a *Magnolia denudata* leaves-derived carbon material doped with two metals, C—Co&Cu$_{0.0001\text{-}24.0}$-700-2.0-2.0-8.0 (immersion in a 0.0001 mol/L solution of salts of Co (II) and Cu (II) for 24 h, carbonization at 700° C. for 2.0 h, and washing with 2.0 mol/L HCl for 8 h), was obtained in an amount of 0.6574 g.

Example 4

A bottom of a weeping willow (*Salix babylonica*) branch with leaves was immersed in an aqueous solution containing 0.000001 mol/L of cobalt (II) acetate and 0.000001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.000001\text{-}24.0}$-700-2.0-2.0-8.0 (immersion in a 0.000001 mol/L solution of salts of Co (II) and Cu (II) for 24.0 h, carbonization at 700° C. for 2.0 h, and washing with 2.0 mol/L HCl for 8.0 h), was obtained in an amount of 0.6318 g.

Example 5

A bottom of a weeping willow (*Salix babylonica*) branch with leaves was immersed in an aqueous solution containing 0.001 mol/L of cobalt (II) acetate and 0.001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.001\text{-}24.0}$-700-2.0-2.0-8.0 (immersion in a 0.001 mol/L solution of salts of Co (II) and Cu (II) for 24.0 h, carbonization at 700° C. for 2.0 h, and washing with 2.0 mol/L HCl for 8.0 h), was obtained in an amount of 0.6343 g.

Example 6

A bottom of a weeping willow (*Salix babylonica*) branch with leaves was immersed in an aqueous solution containing 0.0001 mol/L of iron (II) acetate and 0.0001 mol/L of nickel (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Fe&Ni$_{0.0001\text{-}24.0}$-700-2.0-2.0-8.0 (immersion in a 0.0001 mol/L solution of salts of Fe (II) and Ni (II) for 24.0 h, carbonization at 700° C. for 2.0 h, and washing with 2.0 mol/L HCl for 8.0 h), was obtained in an amount of 0.6471 g.

Example 7

A bottom of a weeping willow (*Salix babylonica*) branch with leaves was immersed in an aqueous solution containing 0.0001 mol/L of manganese (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Mn&Cu$_{0.0001\text{-}24.0}$-700-2.0-2.0-8.0 (immersion in a 0.0001 mol/L solution of salts of Mn (II) and Cu (II) for 24.0 h, carbonization at 700° C. for 2.0 h, and washing with 2.0 mol/L HCl for 8.0 h), was obtained in an amount of 0.6427 g.

Example 8

A bottom of a weeping willow (*Salix babylonica*) branch with leaves was immersed in an aqueous solution containing 0.0001 mol/L of cobalt (II) acetate and 0.0001 mol/L of zinc (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Zn$_{0.0001-24.0}$-700-2.0-2.0-8.0 (immersion in a 0.0001 mol/L solution of salts of Co (II) and Zn (II) for 24.0 h, carbonization at 700° C. for 2.0 h, and washing with 2.0 mol/L HCl for 8.0 h), was obtained in an amount of 0.6356 g.

Example 9

A bottom of a weeping willow (*Salix babylonica*) branch with leaves was immersed in an aqueous solution containing 0.0001 mol/L of iron (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Fe&Cu$_{0.0001-24.0}$-700-2.0-2.0-8.0 (immersion in a 0.0001 mol/L solution of salts of Fe (II) and Cu (II) for 24 h, carbonization at 700° C. for 2.0 h, and washing with 2.0 mol/L HCl for 8.0 h), was obtained in an amount of 0.6392 g.

Example 10

A bottom of a weeping willow (*Salix babylonica*) branch with leaves was immersed in an aqueous solution containing 0.0001 mol/L of cobalt (II) acetate and 0.0001 mol/L of copper (II) acetate for 1.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-1.0}$-700-2.0-2.0-8.0 (immersion in a 0.0001 mol/L solution of salts of Fe (II) and Cu (II) for 1.0 h, carbonization at 700° C. for 2.0 h, and washing with 2.0 mol/L HCl for 8.0 h), was obtained in an amount of 0.5947 g.

Example 11

A bottom of a weeping willow (*Salix babylonica*) branch with leaves was immersed in an aqueous solution containing 0.0001 mol/L of cobalt (II) acetate and 0.0001 mol/L of copper (II) acetate for 12.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-12.0}$-700-2.0-2.0-8.0 (immersion in a 0.0001 mol/L solution of salts of Co (II) and Cu (II) for 12.0 h, carbonization at 700° C. for 2.0 h, and washing with 2.0 mol/L HCl for 8.0 h), was obtained in an amount of 0.6215 g.

Example 12

A bottom of a weeping willow (*Salix babylonica*) branch with leaves was immersed in an aqueous solution containing 0.0001 mol/L of cobalt (II) acetate and 0.0001 mol/L of copper (II) acetate for 36.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-36.0}$-700-2.0-2.0-8.0 (immersion in a 0.0001 mol/L solution of salts of Co (II) and Cu (II) for 36.0 h, carbonization at 700° C. for 2.0 h, and washing with 2.0 mol/L HCl for 8.0 h), was obtained in an amount of 0.6634 g.

Example 13

A bottom of a weeping willow (*Salix babylonica*) branch with leaves was immersed in an aqueous solution containing 0.0001 mol/L of cobalt (II) acetate and 0.0001 mol/L of copper (II) acetate for 48.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-48.0}$-700-2.0-2.0-8.0 (immersion in a 0.0001 mol/L solution of salts of Co (II) and Cu (II) for 48.0 h, carbonization at 700° C. for 2.0 h, and washing with 2.0 mol/L HCl for 8.0 h), was obtained in an amount of 0.6751 g.

Example 14

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 300° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-300-2.0-2.0-8.0 (immersion in a 0.0001 mol/L solution of salts of Co (II) and Cu (II) for 24 h, carbonization at 300° C. for 2.0 h, and washing with 2.0 mol/L HCl for 8.0 h), was obtained in an amount of 0.6319 g.

Example 15

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 500° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-500-2.0-2.0-8.0 (immersion in a 0.0001 mol/L solution of slats of Co (II) and Cu (II) for 24.0 h, carbonization at 500° C. for 2.0 h, and washing with 2.0 mol/L HCl for 8.0 h), was obtained in an amount of 0.6436 g.

Example 16

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 900° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-900-2.0-2.0-8.0 (immersion in a 0.0001 mol/L solution of salts of Co (II) and Cu (II) for 24.0 h, carbonization at 900° C. for 2.0 h, and washing with 2.0 mol/L HCl for 8.0 h), was obtained in an amount of 0.6347 g.

Example 17

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 1000° C. in a nitrogen atmosphere for 2.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-1000-2.0-2.0-8.0 (immersion in a 0.0001 mol/L solution of salts of Co (II) and Cu (II) for 24.0 h, carbonization at 1000° C. for 2.0 h, and washing with 2.0 mol/L HCl for 8.0 h), was obtained in an amount of 0.6192 g.

Example 18

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 1.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-700-1.0-2.0-8.0 (immersion in a 0.0001 mol/L solution of slats of Co (II) and Cu (II) for 24.0 h, carbonization at 700° C. for 1.0 h, and washing with 2.0 mol/L HCl for 8.0 h), was obtained in an amount of 0.6428 g.

Example 19

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 3.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-700-3.0-2.0-8.0 (immersion in a 0.0001 mol/L solution of salts of Co (II) and Cu (II) for 24.0 h, carbonization at 700° C. for 3.0 h, and washing with 2.0 mol/L HCl for 8.0 h), was obtained in an amount of 0.6396 g.

Example 20

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 4.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-700-4.0-2.0-8.0 (immersion in a 0.0001 mol/L solution of salts of Co (II) and Cu (II) for 24.0 h, carbonization at 700° C. for 4.0 h, and washing with 2.0 mol/L HCl for 8.0 h), was obtained in an amount of 0.6272 g.

Example 21

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 5.0 h. After being cooled to room temperature, the leaves were ground to a powder. 2.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-700-5.0-2.0-8.0 (immersion in a 0.0001 mol/L solution of salts of Co (II) and Cu (II) for 24.0 h, carbonization at 700° C. for 5.0 h, and washing with 2.0 mol/L HCl for 8.0 h), was obtained in an amount of 0.6149 g.

Example 22

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 1.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-700-2.0-1.0-8.0 (immersion in a 0.0001 mol/L solution of salts of Co (II) and Cu (II) for 24.0 h, carbonization at 700° C. for 2.0 h, and washing with 1.0 mol/L HCl for 8.0 h), was obtained in an amount of 0.6625 g.

Example 23

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 3.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-700-2.0-3.0-8.0 (immersion in a 0.0001 mol/L solution of salts of Co (II) and Cu(II) for 24 h, carbonization at 700° C. for 2.0 h, and washing with 3.0 mol/L HCl for 8.0 h), was obtained in an amount of 0.6413 g.

Example 24

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 4.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-700-2.0-4.0-8.0 (immersion in a 0.0001 mol/L solution of salts of Co (II) and Cu (II) for 24.0 h, carbonization at 700° C. for 2.0 h, and washing with 4.0 mol/L HCl for 8.0 h), was obtained in an amount of 0.6286 g.

Example 25

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 5.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-700-2.0-5.0-8.0 (immersion in a 0.0001 mol/L solution of salts of Co (II) and Cu (II) for 24.0 h, carbonization at 700° C. for 2.0 h, and washing with 5.0 mol/L HCl for 8.0 h), was obtained in an amount of 0.6134 g.

Example 26

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 4.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-700-2.0-2.0-4.0 (immersion in a 0.0001 mol/L solution of salts of Co (II) and Cu(II) for 24.0 h, carbonization at 700° C. for 2.0 h, and washing with 2.0 mol/L HCl for 4.0 h), was obtained in an amount of 0.6839 g.

Example 27

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 6.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-700-2.0-2.0-6.0 (immersion in a 0.0001 mol/L solution of salts of Co (II) and Cu(II) for 24.0 h, carbonization at 700° C. for 2.0 h, and washing with 2.0 mol/L HCl for 6.0 h), was obtained in an amount of 0.6723 g.

Example 28

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 10.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-700-2.0-2.0-10.0 (immersion in a 0.0001 mol/L solution of Co (II) and Cu (II) for 24.0 h, carbonization at 700° C. for 2.0 h, and washing with 2.0 mol/L HCl for 10.0 h), was obtained in an amount of 0.6348 g.

Example 29

A bottom of a weeping willow (*Salix babylonica*) branch with leaves was immersed in an aqueous solution containing 0.0001 mol/L of cobalt (II) acetate and 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 2.0 mol/L of a HCl aqueous solution was added to the powder and stirred for 12.0 h at room temperature, followed by suction filtration, washing until neutral with water, and vacuum drying at 100° C. for 2.0 h. As a result, a weeping willow leaves-derived carbon material doped with two metals, C—Co&Cu$_{0.0001-24.0}$-700-2.0-2.0-12.0 (immersion in a 0.0001 mol/L solution of salts of Co (II) and Cu (II) for 24.0 h, carbonization at 700° C. for 2.0 h, and washing with 2.0 mol/L HCl for 12.0 h), was obtained in an amount of 0.6193 g.

Example 30

0.020 g of the carbon material prepared in Example 1 (C—Co&Cu$_{0.0001-24.0}$-700-2.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 8.0 h. After completion of the reaction, the reaction mixture was allowed to cool to room temperature. 1.3115 g (5.00 mmol) of pph3 was added thereto and the mixture was stirred for 30 min at room temperature in order to allow the peroxide formed during the reaction to be reduced. Analysis of the reaction products was then carried out. The analysis showed that the conversion of cyclohexane was 6.03%, the selectivity for cyclohexanol was 44.78%, the selectivity for cyclohexanone was 47.72%, the selectivity for cyclohexyl hydroperoxide was 5.53%, the selectivity for adipic acid was 1.02%, and the selectivity for glutaric acid was 0.95%.

Example 31

0.0200 g of the carbon material prepared in Example 2 (C—Co&Cu$_{0.0001-24.0}$-700-2.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 8.0 h. After completion of the reaction, the reaction mixture was allowed to cool to room temperature. 1.3115 g (5.00 mmol) of pph3 was added thereto and the mixture was stirred for 30 min at room temperature in order to allow the peroxide formed during the reaction to be reduced. Analysis of the reaction products was then carried out. The analysis showed that the conversion of cyclohexane was 6.83%, the selectivity for cyclohexanol was 45.32%, the selectivity for cyclohexanone was 46.85%, the selectivity for cyclohexyl hydroperoxide was 4.48%, the selectivity for adipic acid was 1.72%, and the selectivity for glutaric acid was 1.63%.

Example 32

0.0200 g of the carbon material prepared in Example 3 (C—Co&Cu$_{0.0001-24.0}$-700-2.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 8.0 h. After completion of the reaction, the reaction mixture was allowed to cool to room temperature. 1.3115 g (5.00 mmol) of pph3 was added thereto and the mixture was stirred for 30 min at room temperature in order to allow the peroxide formed during the reaction to be reduced. Analysis of the reaction products was then carried out. The analysis showed that the conversion of cyclohexane was 7.63%, the selectivity for cyclohexanol was 47.93%, the selectivity for cyclohexanone was 49.51%, the selectivity for cyclohexyl hydroperoxide was 1.47%, the selectivity for adipic acid was 0.62%, and the selectivity for glutaric acid was 0.47%.

Example 33

0.02000 g of the carbon material prepared in Example 6 (C—Fe&Ni$_{0.0001-24.0}$-700-2.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 8.0 h. After completion of the reaction, the reaction mixture was allowed to cool to room temperature. 1.3115 g (5.00 mmol) of pph3 was added thereto and the mixture was stirred for 30 min at room temperature in order to allow the peroxide formed during the reaction to be reduced. Analysis of the reaction products was then carried out. The analysis showed that the conversion of cyclohexane was 7.95%, the selectivity for cyclohexanol was 46.58%, the selectivity for cyclohexanone was 47.76%, the selectivity for cyclohexyl hydroperoxide was 4.83%, the selectivity for adipic acid was 0.51%, and the selectivity for glutaric acid was 0.32%.

Example 34

0.02000 g of the carbon material prepared in Example 7 (C—Mn&Cu$_{0.0001-24.0}$-700-2.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 8.0 h. After completion of the reaction, the reaction mixture was allowed to cool to room temperature. 1.3115 g (5.00 mmol) of pph3 was added thereto and the mixture was stirred for 30 min at room temperature in order to allow the peroxide formed during the reaction to be reduced. Analysis of the reaction products was then carried out. The analysis showed that the conversion of cyclohexane was 7.53%, the selectivity for cyclohexanol was 44.29%, the selectivity for cyclohexanone was 45.62%, the selectivity for cyclohexyl hydroperoxide was 5.43%, the selectivity for adipic acid was 2.97%, and the selectivity for glutaric acid was 1.69%.

Example 35

0.0200 g of the carbon material prepared in Example 5 (C—Co&Cu$_{0.001-24.0}$-700-2.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 600 rpm and reacted at 120° C. and 1.00 MPa for 8.0 h. After completion of the reaction, the reaction mixture was allowed to cool to room temperature. 1.3115 g (5.00 mmol) of pph3 was added thereto and the mixture was stirred for 30 min at room temperature in order to allow the peroxide formed during the reaction to be reduced. Analysis of the reaction products was then carried out. The analysis showed that the conversion of cyclohexane was 6.48%, the selectivity for cyclohexanol was 45.36%, the selectivity for cyclohexanone was 48.73%, the selectivity for cyclohexyl hydroperoxide was 4.49%, the selectivity for adipic acid was 1.04%, and the selectivity for glutaric acid was 0.38%.

Example 36

0.0200 g of the carbon material prepared in Example 8 (C—Co&Zn$_{0.0001-24.0}$-700-2.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 1000 rpm and reacted at 120° C. and 1.00 MPa for 8.0 h. After completion of the reaction, the reaction mixture was allowed to cool to room temperature. 1.3115 g (5.00 mmol) of pph3 was added thereto and the mixture was stirred for 30 min at room temperature in order to allow the peroxide formed during the reaction to be reduced. Analysis of the reaction products was then carried out. The analysis showed that the conversion of cyclohexane was 7.23%, the selectivity for cyclohexanol was 44.68%, the selectivity for cyclohexanone was 47.91%, the selectivity for cyclohexyl hydroperoxide was 5.22%, the selectivity for adipic acid was 1.43%, and the selectivity for glutaric acid was 0.76%.

Example 37

0.0200 g of the carbon material prepared in Example 9 (C—Fe&Cu$_{0.0001-24.0}$-700-2.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 1200 rpm and reacted at 120° C. and 1.00 MPa for 8.0 h. After completion of the reaction, the reaction mixture was allowed to cool to room temperature. 1.3115 g (5.00 mmol) of pph3 was added thereto and the mixture was stirred for 30 min at room temperature in order to allow the peroxide formed during the reaction to be reduced. Analysis of the reaction products was then carried out. The analysis showed that the conversion of cyclohexane was 7.44%, the selectivity for cyclohexanol was 43.87%, the selectivity for cyclohexanone was 46.99%, the selectivity for cyclohexyl hydroperoxide was 5.27%, the selectivity for adipic acid was 2.65%, and the selectivity for glutaric acid was 1.22%.

Example 38

0.0200 g of the carbon material prepared in Example 28 (C—Co&Cu$_{0.0001-24.0}$-700-2.0-2.0-10.0) was dispersed in 16.8320 g (200 mmol) of cyclohexane inside a 100 mL Teflon-lined stainless steel autoclave, and the autoclave was then sealed. The mixture was heated to 80° C. with stirring. Oxygen was introduced into the autoclave until a pressure of 1.00 MPa was reached. Then, the mixture was stirred at a stirring speed of 800 rpm and reacted at 80° C. and 1.00 MPa for 8.0 h. After completion of the reaction, the reaction mixture was allowed to cool to room temperature. 1.3115 g (5.00 mmol) of pph3 was added thereto and the mixture was stirred for 30 min at room temperature in order to allow the peroxide formed during the reaction to be reduced. Analysis of the reaction products was then carried out. The analysis showed that the conversion of cyclohexane was 5.91%, the selectivity for cyclohexanol was 42.54%, the selectivity for cyclohexanone was 47.29%, the selectivity for cyclohexyl hydroperoxide was 7.91%, the selectivity for adipic acid was 1.06%, and the selectivity for glutaric acid was 1.20%.

Example 39

0.0200 g of the carbon material prepared in Example 11 (C—Co&Cu$_{0.0001-12.0}$-700-2.0-2.0-8.0) was dispersed in 16.8320 g (200 mmol) of cyclohexane inside a 100 mL Teflon-lined stainless steel autoclave, and the autoclave was then sealed. The mixture was heated to 100° C. with stirring. Oxygen was introduced into the autoclave until a pressure of 1.00 MPa was reached. Then, the mixture was stirred at a stirring speed of 800 rpm and reacted at 100° C. and 1.00 MPa for 8.0 h. After completion of the reaction, the reaction mixture was allowed to cool to room temperature. 1.3115 g (5.00 mmol) of pph3 was added thereto and the mixture was stirred for 30 min at room temperature in order to allow the peroxide formed during the reaction to be reduced. Analysis of the reaction products was then carried out. The analysis showed that the conversion of cyclohexane was 6.84%, the selectivity for cyclohexanol was 45.82%, the selectivity for cyclohexanone was 45.63%, the selectivity for cyclohexyl hydroperoxide was 5.37%, the selectivity for adipic acid was 1.70%, and the selectivity for glutaric acid was 1.48%.

Example 40

0.0200 g of the carbon material prepared in Example 12 (C—Co&$Cu_{0.0001-36.0}$-700-2.0-2.0-8.0) was dispersed in 16.8320 g (200 mmol) of cyclohexane inside a 100 mL Teflon-lined stainless steel autoclave, and the autoclave was then sealed. The mixture was heated to 140° C. with stirring. Oxygen was introduced into the autoclave until a pressure of 1.00 MPa was reached. Then, the mixture was stirred at a stirring speed of 800 rpm and reacted at 140° C. and 1.00 MPa for 8.0 h. After completion of the reaction, the reaction mixture was allowed to cool to room temperature. 1.3115 g (5.00 mmol) of pph3 was added thereto and the mixture was stirred for 30 min at room temperature in order to allow the peroxide formed during the reaction to be reduced. Analysis of the reaction products was then carried out. The analysis showed that the conversion of cyclohexane was 7.87%, the selectivity for cyclohexanol was 44.05%, the selectivity for cyclohexanone was 43.97%, the selectivity for cyclohexyl hydroperoxide was 5.91%, the selectivity for adipic acid was 3.22%, and the selectivity for glutaric acid was 2.85%.

Example 41

0.0200 g of the carbon material prepared in Example 13 (C—Co&$Cu_{0.0001-48.0}$-700-2.0-2.0-8.0) was dispersed in 16.8320 g (200 mmol) of cyclohexane inside a 100 mL Teflon-lined stainless steel autoclave, and the autoclave was then sealed. The mixture was heated to 160° C. with stirring. Oxygen was introduced into the autoclave until a pressure of 1.00 MPa was reached. Then, the mixture was stirred at a stirring speed of 800 rpm and reacted at 160° C. and 1.00 MPa for 8.0 h. After completion of the reaction, the reaction mixture was allowed to cool to room temperature. 1.3115 g (5.00 mmol) of pph3 was added thereto and the mixture was stirred for 30 min at room temperature in order to allow the peroxide formed during the reaction to be reduced. Analysis of the reaction products was then carried out. The analysis showed that the conversion of cyclohexane was 8.05%, the selectivity for cyclohexanol was 43.38%, the selectivity for cyclohexanone was 43.14%, the selectivity for cyclohexyl hydroperoxide was 6.69%, the selectivity for adipic acid was 3.53%, and the selectivity for glutaric acid was 3.26%.

Example 42

0.0200 g of the carbon material prepared in Example 14 (C—Co&$Cu_{0.0001-24.0}$-300-2.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 0.10 MPa was reached. Then, the mixture was stirred at a stirring speed of 800 rpm and reacted at 120° C. and 0.10 MPa for 8.0 h. After completion of the reaction, the reaction mixture was allowed to cool to room temperature. 1.3115 g (5.00 mmol) of pph3 was added thereto and the mixture was stirred at room temperature for 30 min in order to allow the peroxide formed during the reaction to be reduced. Analysis of the reaction products was then carried out. The analysis showed that the conversion of cyclohexane was 3.58%, the selectivity for cyclohexanol was 43.71%, the selectivity for cyclohexanone was 49.08%, the selectivity for cyclohexyl hydroperoxide was 6.14%, the selectivity for adipic acid was 0.60%, and the selectivity for glutaric acid was 0.47%.

Example 43

0.0200 g of the carbon material prepared in Example 15 (C—Co&$Cu_{0.0001-24.0}$-500-2.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 0.50 MPa was reached. Then, the mixture was stirred at a stirring speed of 800 rpm and reacted at 120° C. and 0.50 MPa for 8.0 h. After completion of the reaction, the reaction mixture was allowed to cool to room temperature. 1.3115 g (5.00 mmol) of pph3 was added thereto and the mixture was stirred at room temperature for 30 min in order to allow the peroxide formed during the reaction to be reduced. Analysis of the reaction products was then carried out. The analysis showed that the conversion of cyclohexane was 6.73%, the selectivity for cyclohexanol was 45.65%, the selectivity for cyclohexanone was 48.82%, the selectivity for cyclohexyl hydroperoxide was 4.39%, the selectivity for adipic acid was 0.53%, and the selectivity for glutaric acid was 0.61%.

Example 44

0.0200 g of the carbon material prepared in Example 16 (C—Co&$Cu_{0.0001-24.0}$-900-2.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 1.50 MPa was reached. Then, the mixture was stirred at a stirring speed of 800 rpm and reacted at 120° C. and 1.50 MPa for 8.0 h. After completion of the reaction, the reaction mixture was allowed to cool to room temperature. 1.3115 g (5.00 mmol) of pph3 was added thereto and the mixture was stirred at room temperature for 30 min in order to allow the peroxide formed during the reaction to be reduced. Analysis of the reaction products was then carried out. The analysis showed that the conversion of cyclohexane was 7.25%, the selectivity for cyclohexanol was 44.97%, the selectivity for cyclohexanone was 46.74%, the selectivity for cyclohexyl hydroperoxide was 5.02%, the selectivity for adipic acid was 1.56%, and the selectivity for glutaric acid was 1.71%.

Example 45

0.0200 g of the carbon material prepared in Example 17 (C—Co&$Cu_{0.0001-24.0}$-1000-2.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 2.00 MPa was reached. Then, the mixture was stirred at a stirring speed of 800 rpm and reacted at 120° C. and 2.00 MPa for 8.0 h. After completion of the reaction, the reaction mixture was allowed to cool to room temperature. 1.3115 g (5.00 mmol) of pph3 was added thereto and the mixture was stirred at room temperature for 30 min in order to allow the peroxide formed during the reaction to be reduced. Analysis of the reaction products was then carried out. The analysis showed that the conversion of cyclohexane was 7.01%, the selectivity for cyclohexanol was 43.83%, the selectivity for cyclohexanone was 46.15%, the selectivity for cyclohexyl hydroperoxide was 4.67%, the selectivity for adipic acid was 2.92%, and the selectivity for glutaric acid was 2.43%.

Example 46

0.0200 g of the carbon material prepared in Example 18 (C—Co&Cu$_{0.0001\text{-}24.0}$-700-1.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 2.0 h. After completion of the reaction, the reaction mixture was allowed to cool to room temperature. 1.3115 g (5.00 mmol) of pph3 was added thereto and the mixture was stirred at room temperature for 30 min in order to allow the peroxide formed during the reaction to be reduced. Analysis of the reaction products was then carried out. The analysis showed that the conversion of cyclohexane was 3.93%, the selectivity for cyclohexanol was 40.31%, the selectivity for cyclohexanone was 48.59%, the selectivity for cyclohexyl hydroperoxide was 7.65%, the selectivity for adipic acid was 2.08%, and the selectivity for glutaric acid was 1.37%.

Example 47

0.0200 g of the carbon material prepared in Example 19 (C—Co&Cu$_{0.0001\text{-}24.0}$-700-3.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 16.0 h. After completion of the reaction, the reaction mixture was allowed to cool to room temperature. 1.3115 g (5.00 mmol) of pph3 was added thereto and the mixture was stirred at room temperature for 30 min in order to allow the peroxide formed during the reaction to be reduced. Analysis of the reaction products was then carried out. The analysis showed that the conversion of cyclohexane was 7.86%, the selectivity for cyclohexanol was 43.44%, the selectivity for cyclohexanone was 45.15%, the selectivity for cyclohexyl hydroperoxide was 5.98%, the selectivity for adipic acid was 3.26%, and the selectivity for glutaric acid was 2.17%.

Example 48

0.0200 g of the carbon material prepared in Example 20 (C—Co&Cu$_{0.0001\text{-}24.0}$-700-4.0-2.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 24.0 h. After completion of the reaction, the reaction mixture was allowed to cool to room temperature. 1.3115 g (5.00 mmol) of pph3 was added thereto and the mixture was stirred at room temperature for 30 min in order to allow the peroxide formed during the reaction to be reduced. Analysis of the reaction products was then carried out. The analysis showed that the conversion of cyclohexane was 8.19%, the selectivity for cyclohexanol was 42.28%, the selectivity for cyclohexanone was 44.63%, the selectivity for cyclohexyl hydroperoxide was 6.86%, the selectivity for adipic acid was 3.01%, and the selectivity for glutaric acid was 3.22%.

Example 49

0.0200 g of the carbon material prepared in Example 21 (C—Co&Cu$_{0.0001\text{-}24.0}$-700-5.0-2.0-8.0) was dispersed in 14.0280 g (200 mmol) of cyclopentane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 8.0 h. After completion of the reaction, the reaction mixture was allowed to cool to room temperature. 1.3115 g (5.00 mmol) of pph3 was added thereto and the mixture was stirred at room temperature for 30 min in order to allow the peroxide formed during the reaction to be reduced. Analysis of the reaction products was then carried out. The analysis showed that the conversion of cyclopentane was 7.04%, the selectivity for cyclopentanol was 42.45%, the selectivity for cyclopentanone was 52.24%, the selectivity for cyclopentyl hydroperoxide was 3.06%, the selectivity for glutaric acid was 1.32%, and the selectivity for succinic acid was 0.93%.

Example 50

0.0200 g of the carbon material prepared in Example 22 (C—Co&Cu$_{0.0001\text{-}24.0}$-700-2.0-1.0-8.0) was dispersed in 19.6380 g (200 mmol) of cycloheptane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 8.0 h. After completion of the reaction, the reaction mixture was allowed to cool to room temperature. 1.3115 g (5.00 mmol) of pph3 was added thereto and the mixture was stirred at room temperature for 30 min in order to allow the peroxide formed during the reaction to be reduced. Analysis of the reaction products was then carried out. The analysis showed that the conversion of cycloheptane was 7.14%, the selectivity for cycloheptanol was 39.86%, the selectivity for cycloheptanone was 56.59%, the selectivity for cycloheptyl hydroperoxide was 2.39%, the selectivity for pimelic acid was 0.75%, and the selectivity for adipic acid was 0.41%.

Example 51

0.0200 g of the carbon material prepared in Example 23 (C—Co&Cu$_{0.0001\text{-}24.0}$-700-2.0-3.0-8.0) was dispersed in 22.4440 g (200 mmol) of cyclooctane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 8.0 h. After completion of the reaction, the reaction mixture was allowed to cool to room temperature. 1.3115 g (5.00 mmol) of pph3 was added thereto and the mixture was stirred at room temperature for 30 min in order to allow the peroxide formed during the reaction to be reduced. Analysis of the reaction products was then carried out. The analysis showed that the conversion of cyclooctane was 7.62%, the selectivity for cyclooctanol was 46.44%, the selectivity for cyclooctanone was 50.75%, the selectivity for cyclooctyl hydroperoxide was 1.36%, the selectivity for octanedioic acid was 0.87%, and the selectivity for heptanedioic acid was 0.58%.

Example 52

0.0200 g of the carbon material prepared in Example 24 (C—Co&Cu$_{0.0001-24.0}$-700-2.0-4.0-8.0) was dispersed in 33.6640 g (200 mmol) of cyclododecane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 8.0 h. After completion of the reaction, the reaction mixture was allowed to cool to room temperature. 1.3115 g (5.00 mmol) of pph3 was added thereto and the mixture was stirred at room temperature for 30 min in order to allow the peroxide formed during the reaction to be reduced. Analysis of the reaction products was then carried out. The analysis showed that the conversion of cyclododecane was 7.26%, the selectivity for cyclododecanol was 46.82%, the selectivity for cyclododecanone was 48.57%, and the selectivity for cyclododecyl hydroperoxide was 4.61%. No formation of dodecanoic acid and undecanoic acid was observed.

Example 53 (Comparative Example)

A bottom of a weeping willow (*Salix babylonica*) branch with leaves was immersed in an aqueous solution containing 0.0001 mol/L of cobalt (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 3.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with a single metal, C—Co$_{0.0001-24.0}$-700-2.0-3.0-8.0 (immersion in a 0.0001 mol/L solution of a Co (II) salt for 24 h, carbonization at 700° C. for 2.0 h, and washing with 3.0 mol/L HCl for 8.0 h), was obtained in an amount of 0.6413 g.

0.0200 g of the carbon material prepared in this Example (C—Co$_{0.0001-24.0}$-700-2.0-3.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 8.0 h. After completion of the reaction, the reaction mixture was allowed to cool to room temperature. 1.3115 g (5.00 mmol) of pph3 was added thereto and the mixture was stirred for 30 min at room temperature in order to allow the peroxide formed during the reaction to be reduced. Analysis of the reaction products was then carried out. The analysis showed that the conversion of cyclohexane was 2.19%, the selectivity for cyclohexanol was 46.59%, the selectivity for cyclohexanone was 48.74%, the selectivity for cyclohexyl hydroperoxide was 2.38%, the selectivity for adipic acid was 1.42%, and the selectivity for glutaric acid was 0.87%.

Example 54 (Comparative Example)

A bottom of a weeping willow (*Salix babylonica*) branch with leaves was immersed in an aqueous solution containing 0.0001 mol/L of copper (II) acetate for 24.0 h. After immersion, the leaves (about 2.00 g) were removed from the branch and washed with water. Then, the leaves were carbonized at 700° C. in a nitrogen atmosphere for 2.0 h. After being cooled to room temperature, the leaves were ground to a powder. 3.0 mol/L of a HCl aqueous solution was added to the powder and stirred for 8.0 h at room temperature, followed by suction filtration, washing until neutral with water, and vacuum drying at 100° C. for 2.0 h. As a result, a weeping willow leaves-derived carbon material doped with a single metal, C—Cu$_{0.0001-24.0}$-700-2.0-3.0-8.0 (immersion in a 0.0001 mol/L solution of a Cu(II) salt for 24.0 h, carbonization at 700° C. for 2.0 h, and washing with 3.0 mol/L HCl for 8.0 h), was obtained in an amount of 0.6413 g.

0.0200 g of the carbon material prepared in this Example (C—Cu$_{0.0001-24.0}$-700-2.0-3.0-8.0) was dispersed in 16.8320 g (200 mmol) of cyclohexane inside a 100 mL Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 8.0 h. After completion of the reaction, the reaction mixture was allowed to cool to room temperature. 1.3115 g (5.00 mmol) of pph3 was added thereto and the mixture was stirred at room temperature for 30 min in order to allow the peroxide formed during the reaction to be reduced. Analysis of the reaction products was then carried out. The analysis showed that the conversion of cyclohexane was 2.57%, the selectivity for cyclohexanol was 44.89%, the selectivity for cyclohexanone was 50.64%, the selectivity for cyclohexyl hydroperoxide was 2.51%, the selectivity for adipic acid was 1.25%, and the selectivity for glutaric acid was 0.71%.

Example 55 (Lager Scale)

0.2000 g of the carbon material prepared in Example 27 (C—Co&Cu$_{0.0001-24.0}$-700-2.0-2.0-6.0) was dispersed in 168.320 g (2 mol) of cyclohexane inside a 1 L Teflon-lined stainless steel autoclave, and the autoclave was then sealed. The mixture was heated to 120° C. with stirring. Oxygen was introduced into the autoclave until a pressure of 1.00 MPa was reached. Then, the mixture was stirred at a stirring speed of 800 rpm and reacted at 120° C. and 1.00 MPa for 8.0 h. After completion of the reaction, the reaction mixture was allowed to cool to room temperature. 13.115 g (50.00 mmol) of pph3 was added thereto and the mixture was stirred at room temperature for 50 min in order to allow the peroxide formed during the reaction to be reduced. Analysis of the reaction products was then carried out. The analysis showed that the conversion of cyclohexane was 7.98%, the selectivity for cyclohexanol was 48.92%, the selectivity for cyclohexanone was 49.71%, the selectivity for adipic acid was 0.87%, and the selectivity for glutaric acid was 0.50%.

The present disclosure has been described above with reference to the examples, which, however, are not exhaustive and should not be construed as limiting the disclosure.

What is claimed is:

1. A method for preparing plant leaves-derived carbon material doped with two metals, prepared by carbonizing, in an inert atmosphere, plant leaves which have absorbed ions of two metals M1 and M2, the method comprising:
   immersing a bottom of a branch with the plant leaves in an aqueous solution of metal salts of the metals M1 and M2 for a period of time, followed by removal of the leaves from the branch and washing with fresh water;
   carbonizing the leaves in a nitrogen atmosphere, followed by cooling the carbonized leaves to room temperature and then grinding the carbonized leaves after being cooled to a powder; and
   washing the powder by stirring the powder in a volume of a hydrochloric acid solution in order to remove inorganic salts therefrom, followed by suction filtration, washing until neutral with water, and drying;
   wherein, the metal M1 is Co, Mn, or Fe, and the metal M2 is Ni, Cu, or Zn; and
   wherein, the leaves are derived from at least one tree selected from the group consisting of *Salix babylonica, Firmiana simplex, Magnolia denudata, Osmanthus, Viburnum odoratissimum, Ginkgo biloba, PopulusL.*, and *Metasequoia glyptostroboides*.

2. The method according to claim 1, wherein, M1 is Co (II), Mn (II), or Fe (II), and wherein, M2 is Ni (II), Cu (II), or Zn (II);
   wherein, Co (II) is provided by any one of, or a mixture of any two or more at any ratio of, $Co(CH_3COO)_2$, $Co(NO_3)_2$, $CoSO_4$, $CoCl_2$, and their hydrates; Mn (II) is provided by any one of, or a mixture of any two or more at any ratio of, $Mn(CH_3COO)_2$, $Mn(NO_3)_2$, $MnSO_4$, $MnCl_2$, and their hydrates; Fe (II) is provided by any one of, or a mixture of any two or more at any ratio of, $Fe(CH_3COO)_2$, $Fe(NO_3)_2$, $FeSO_4$, $FeCl_2$, and their hydrates; Ni (II) is provided by any one of, or a mixture of any two or more at any ratio of, $Ni(CH_3COO)_2$, $Ni(NO_3)_2$, $NiSO_4$, $NiCl_2$, and their hydrates; Cu (II) is provided by any one of, or a mixture of any two or more at any ratio of, $Cu(CH_3COO)_2$, $Cu(NO_3)_2$, $CuSO_4$, $CuCl_2$, and their hydrates; and Zn (II) is provided by any one of, or a mixture of any two or more at any ratio of, $Zn(CH_3COO)_2$, $Zn(NO_3)_2$, $ZnSO_4$, $ZnCl_2$, and their hydrates.

3. The method according to claim 1, wherein the plant leaves-derived carbon material doped with two metals is a catalyst for the oxidation of a cycloalkane.

4. The method according to claim 3, wherein the oxidation of the cycloalkane is performed by a process comprising:
   dispersing the plant leaves-derived carbon material doped with two metals in the cycloalkane to form a mixture, followed by sealing;
   heating the mixture with stirring to a reaction temperature, followed by introducing an oxidant thereinto and stirring for a period of time to allow an oxidation reaction to proceed; and
   after completion of the reaction, cooling the reaction mixture to room temperature, followed by addition of triphenylphosphine and stirring at room temperature for 30 to 40 min to allow a peroxide formed during the oxidation reaction to be reduced.

5. The use method according to claim 4, wherein, the cycloalkane is any one of, or a mixture of any two or more at any ratio of, cyclopentane, cyclohexane, cycloheptane, cyclooctane, cyclononane, cyclodecane, and cyclododecane;
   wherein, the oxidant is oxygen, air, or a mixture thereof at any ratio;
   wherein, the oxidation reaction is conducted at a pressure of 0.1 to 2.0 MPa and a temperature of 80 to 160° C. for 2.0 to 24.0 h, with a stirring speed of 600 to 1200 rpm;
   and wherein, the ratio of the molar amount in mmol of the cycloalkane to the mass in mg of the carbon material is in a range of 5 to 20.

6. The method according to claim 4, wherein, the triphenylphosphine is used in an amount of 2 to 4% by mole, with respect to the total amount of the cycloalkane.

7. A method for preparing plant leaves-derived carbon material doped with two metals, prepared by carbonizing, in an inert atmosphere, plant leaves which have absorbed ions of two metals M1 and M2, the method comprising:
   immersing a bottom of a branch with the plant leaves in an aqueous solution of metal salts of the metals M1 and M2 for a period of time, followed by removal of the leaves from the branch and washing with fresh water;
   carbonizing the leaves in a nitrogen atmosphere, followed by cooling the carbonized leaves to room temperature and then grinding the carbonized leaves after being cooled to a powder; and
   washing the powder by stirring the powder in a volume of a hydrochloric acid solution in order to remove inorganic salts therefrom, followed by suction filtration, washing until neutral with water, and drying;
   wherein, the metal M1 is Co, Mn, or Fe
   wherein, the metal M2 is Ni, Cu, or Zn; and
   wherein, the aqueous solution of metal salts of the metals M1 and M2 has a concentration of the salt of the metal M1 varying from 0.000001 to 0.001 mol/L and a concentration of the salt of the metal M2 varying from 0.000001 to 0.001 mol/L.

8. A method for preparing plant leaves-derived carbon material doped with two metals, prepared by carbonizing, in an inert atmosphere, plant leaves which have absorbed ions of two metals M1 and M2, the method comprising:
   immersing a bottom of a branch with the plant leaves in an aqueous solution of metal salts of the metals M1 and M2 for a period of time, followed by removal of the leaves from the branch and washing with fresh water;
   carbonizing the leaves in a nitrogen atmosphere, followed by cooling the carbonized leaves to room temperature and then grinding the carbonized leaves after being cooled to a powder; and
   washing the powder by stirring the powder in a volume of a hydrochloric acid solution in order to remove inorganic salts therefrom, followed by suction filtration, washing until neutral with water, and drying;
   wherein, the metal M1 is Co, Mn, or Fe
   wherein, the metal M2 is Ni, Cu, or Zn; and
   wherein, the bottom of the branch with the plant leaves is immersed in the aqueous solution of metal salts of the metals M1 and M2 for 1.0 to 48.0 h; wherein, the leaves are carbonized at 300 to 1000° C.for 1.0 to 5.0 h; wherein, the hydrochloric acid solution used to wash the powder is at a concentration of 1.0 to 5.0 mol/L; and wherein, the powder is washed by stirring it in the hydrochloric acid solution for 4.0 to 12.0 h.

* * * * *